(12) United States Patent
Numakawa et al.

(10) Patent No.: US 8,439,677 B2
(45) Date of Patent: May 14, 2013

(54) MAINTENANCE APPARATUS FOR MEDICAL HAND PIECE

(75) Inventors: Makoto Numakawa, Kyoto (JP);
Shigehiko Inoue, Kyoto (JP); Makoto Kawakami, Kyoto (JP); Hirofumi Jikuhara, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 1041 days.

(21) Appl. No.: 10/565,769

(22) PCT Filed: Jul. 23, 2004

(86) PCT No.: PCT/JP2004/010902
§ 371 (c)(1),
(2), (4) Date: Mar. 9, 2006

(87) PCT Pub. No.: WO2005/009271
PCT Pub. Date: Feb. 3, 2005

(65) Prior Publication Data
US 2006/0196728 A1    Sep. 7, 2006

(30) Foreign Application Priority Data
Jul. 25, 2003    (JP) .................................. 2003-280251

(51) Int. Cl.
*A61C 1/00* (2006.01)
*F16N 7/30* (2006.01)
*B08B 9/00* (2006.01)
*C23F 11/00* (2006.01)

(52) U.S. Cl.
USPC ............ 433/104; 184/55.2; 134/166 C; 422/7

(58) Field of Classification Search .......... 433/103–104, 433/114, 229; 422/7; 134/166 C; 184/55.2
See application file for complete search history.

(56) References Cited

U.S. PATENT DOCUMENTS

| | | | | |
|---|---|---|---|---|
| 4,990,087 | A | * | 2/1991 | De Rocchis et al. .......... 433/104 |
| 5,165,503 | A | * | 11/1992 | Hoffman ....................... 433/104 |
| 5,520,882 | A | * | 5/1996 | Brown .......................... 433/104 |

FOREIGN PATENT DOCUMENTS

| | | |
|---|---|---|
| EP | 0 300 945 A2 | 1/1989 |
| JP | 9-56733 | 3/1997 |
| JP | 2587001 | 3/1997 |
| JP | 2001-70319 | 3/2001 |

* cited by examiner

*Primary Examiner* — Heidi M Eide
(74) *Attorney, Agent, or Firm* — DLA Piper LLP (US)

(57) ABSTRACT

The present invention provides a maintenance apparatus for increasing the service life of a medical handpiece. The maintenance apparatus is provided with a first fluid supply which feeds a maintenance fluid to the bearings of a handpiece, capable of rotatably supporting a rotary tool, and a second fluid supply which feeds the maintenance fluid to the chucking structure of the handpiece, capable of detachably holding the rotary tool.

5 Claims, 16 Drawing Sheets

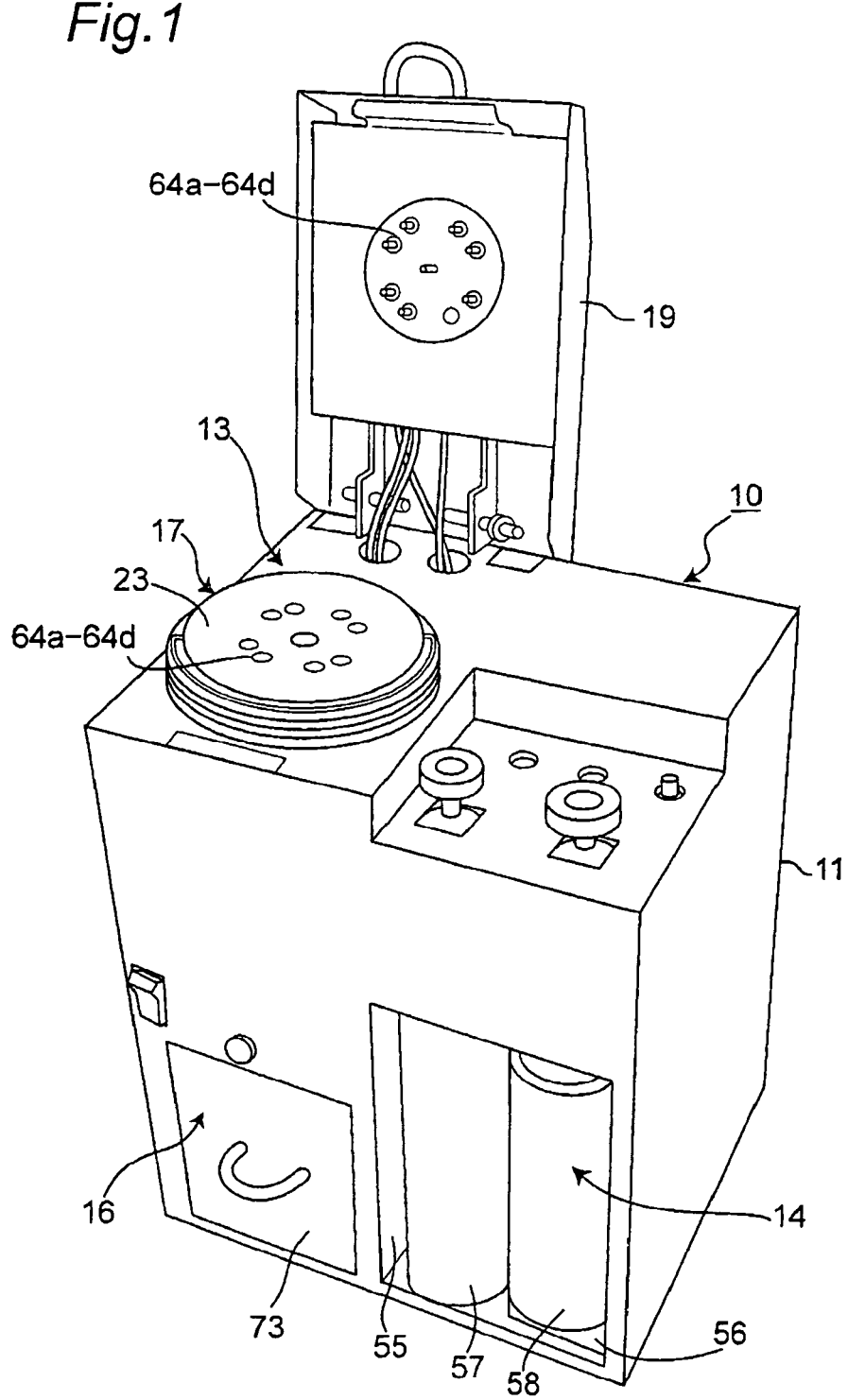

MAINTENANCE APPARATUS FOR MEDICAL HAND PIECE

TECHNICAL FIELD

The present invention relates to a maintenance apparatus for medical handpieces, and particularly to a maintenance apparatus which feeds a liquid, a gas or a mixture thereof to a handpiece equipped with a rotary cutting tool for dental treatment to thereby wash and/or lubricate the handpiece.

BACKGROUND OF THE INVENTION

The existent maintenance apparatuses for dental handpieces are of the type as proposed in Japanese Patent No. 2587001. The apparatus of this type has an adaptor to be connected to the proximal end side of a handpiece so that a washing liquid and a lubricant supplied through the adaptor can be fed to the rotary member of the cutting tool of the handpiece. However, in this maintenance apparatus, the washing liquid and the lubricant supplied to the handpiece are both fed to only the turbine and the bearing thereof, but not to the chucking structure which is located on the center of the turbine and detachably holds the cutting tool, which leads to a problem that the dirt and abrasion filing in the chucking structure can not be removed.

There is another proposal for hand-operation maintenance of medical handpieces, using a special-purpose nozzle equipped on the tip end of a spray bomb. In case of this method, an operator feeds a maintenance fluid to the bearing of a handpiece but pays less attentions to the maintenance of the chucking structure thereof which is very important for safety, than the maintenance of the bearing thereof. Accordingly, the operator feels it troublesome to feed the washing fluid to the chucking structure of the handpiece or often forgets it. Therefore, the maintenance of the chucking structure of the handpiece is not surely carried out. In addition, since the chucking structure is not communicated with the bearing of the handpiece, the maintenance fluid is fed to only the bearing but not to the chucking structure. Further, because the chucking structure made up of a plurality of metallic or resinous components is subject to contamination and foreign matters, such a disadvantage gives serious influence on the function of the chucking structure for holding the cutting tool. When the maintenance fluid is fed to only the bearing in the handpiece, for example, in the air turbine, the bearing can keep its normal high-speed rotation since the maintenance fluid is fed thereto, while the chucking structure tends to deteriorate earlier prior to the bearing, since the maintenance of the chucking structure is insufficient. For this reason, it becomes hard for the chucking structure of the handpiece to firmly hold the cutting tool, which results in a failure in the air turbine. Thus, the air turbine tends to be broken earlier before the handpiece has completed its service life. In another case where a hand-operation maintenance is made on a handpiece, the amount of a maintenance fluid becomes insufficient or excessive, so that the maintenance of the bearing and the chucking structure becomes insufficient, or so that the maintenance thereof costs higher. In addition, feeding an excessive amount of the maintenance fluid induces problems in that such a fluid is adhered to the handpiece so that the operator or an assistant slips one's hand on the grip of the handpiece and fails to hold it, and in that the hand of the operator or the clothes thereof, or the face of a patient or the clothes thereof are stained.

To overcome these problems, the present invention is intended to provide a maintenance apparatus which performs effective and reliable maintenance on the bearing and the chucking structure of a medical handpiece.

DISCLOSURE OF THE INVENTION

To achieve these objects, a maintenance apparatus for a medical handpiece, according to the first embodiment of the present invention, is provided with a first fluid supply which feeds a maintenance fluid to the bearings of a handpiece, capable of rotatably supporting a rotary tool, and a second fluid supply which feeds the maintenance fluid to the chucking structure of the handpiece, capable of detachably holding the rotary tool.

A maintenance apparatus for a medical handpiece, according to the second embodiment of the present invention, is provided with a connector which includes a connector to be detachably connected to a maintenance fluid supply, a first fluid supply which feeds a maintenance fluid supplied to the connector from the maintenance fluid supply, to the bearings of the handpiece, capable of rotatably supporting a rotary tool, and a second fluid supply which feeds the maintenance fluid supplied to the connector from the maintenance fluid supply, to the chucking structure of the handpiece, capable of detachably holding the rotary tool.

A maintenance apparatus according to the third embodiment of the present invention is used for a medical handpiece which comprises a gripping portion and a rotary-tool holding portion formed on one end side of the gripping portion, the gripping portion having a passage which extends from the other end side to the one end side thereof, and the rotary-tool holding portion comprising a chucking structure which detachably holds a rotary tool, a rotatable member which holds the chucking structure and rotates on the center axis of the chucking structure, and bearings which rotatably support the rotatable member, wherein the rotatable member and the rotary tool are rotated by supplied power.

This maintenance apparatus is provided with a first fluid supply to be connected to the other end side of the passage of the gripping portion, and a second fluid supply which is held by the chucking structure, instead of the rotary tool.

A maintenance apparatus for a medical handpiece, according to the fourth embodiment of the present invention, is provided with a fluid supply which feeds a maintenance fluid to the chucking structure of a handpiece, capable of detachably holding a rotary tool, and a control unit which controls the supply of the maintenance fluid to the maintenance apparatus.

In this maintenance apparatus, preferably, the second fluid supply is supported unrotatable. Preferably, the second fluid supply has, at its outer wall, a passage which allows the fluid to flow along the axial direction. Preferably, the second fluid supply has a hole which injects the fluid in the form of mist. Preferably, the control unit which controls the supply of the maintenance fluid to the maintenance apparatus controls not only the feeding of the fluid to the chucking structure of the handpiece but also the feeding of the fluid to the bearings thereof.

According to each of the maintenance apparatuses of the first to the third embodiments of the present invention, the maintenance fluid is automatically fed to the bearings and the chucking structure of the handpiece, and therefore, the washing and lubrication of not only the bearings which rotatably support the rotary tool, but also the chucking structure which detachably holds the rotary tool and which gives a serious influence on the safety of the handpiece can be reliably performed. According to the maintenance apparatus of the fourth embodiment of the present invention, the maintenance fluid is automatically fed to the chucking structure of the handpiece, to which an operator feeds the maintenance fluid, feeling it troublesome, or often forgets such feeding, and therefore, the washing and lubrication of the chucking structure of the handpiece, very important for the safety operation of the handpiece, can be reliably performed. Thus, the dirt and foreign matters (abrasion filing, etc.) of the chucking structure of the handpiece can be removed, and it becomes possible for the chucking structure of the handpiece to reliably hold a rotary tool over a long period of time, without the deterioration thereof. Therefore, the service life of the handpiece including this chucking structure can be increased to the maximum.

Further, the maintenance fluid is supplied just in a required amount, and therefore, there is no disadvantage that the maintenance of the chucking structure of a handpiece becomes insufficient because of the insufficient amount of the supplied maintenance fluid, nor disadvantage that the excessive amount of the supplied maintenance fluid adheres to the handpiece, which leads to an operator's or an assistant's failure in holding the grip thereof because of the slipping of the operator's or the assistant's hand thereon, and to the staining of their hands, faces or clothes, or which leads to a higher cost for the maintenance.

BRIEF DESCRIPTION OF THE DRAWINGS

FIG. 1 is a perspective view of a maintenance apparatus according to the first embodiment of the present invention;

PREFERRED EMBODIMENTS OF THE INVENTION

I. First Embodiment
(1) General Construction of Apparatus

Figure 2A:
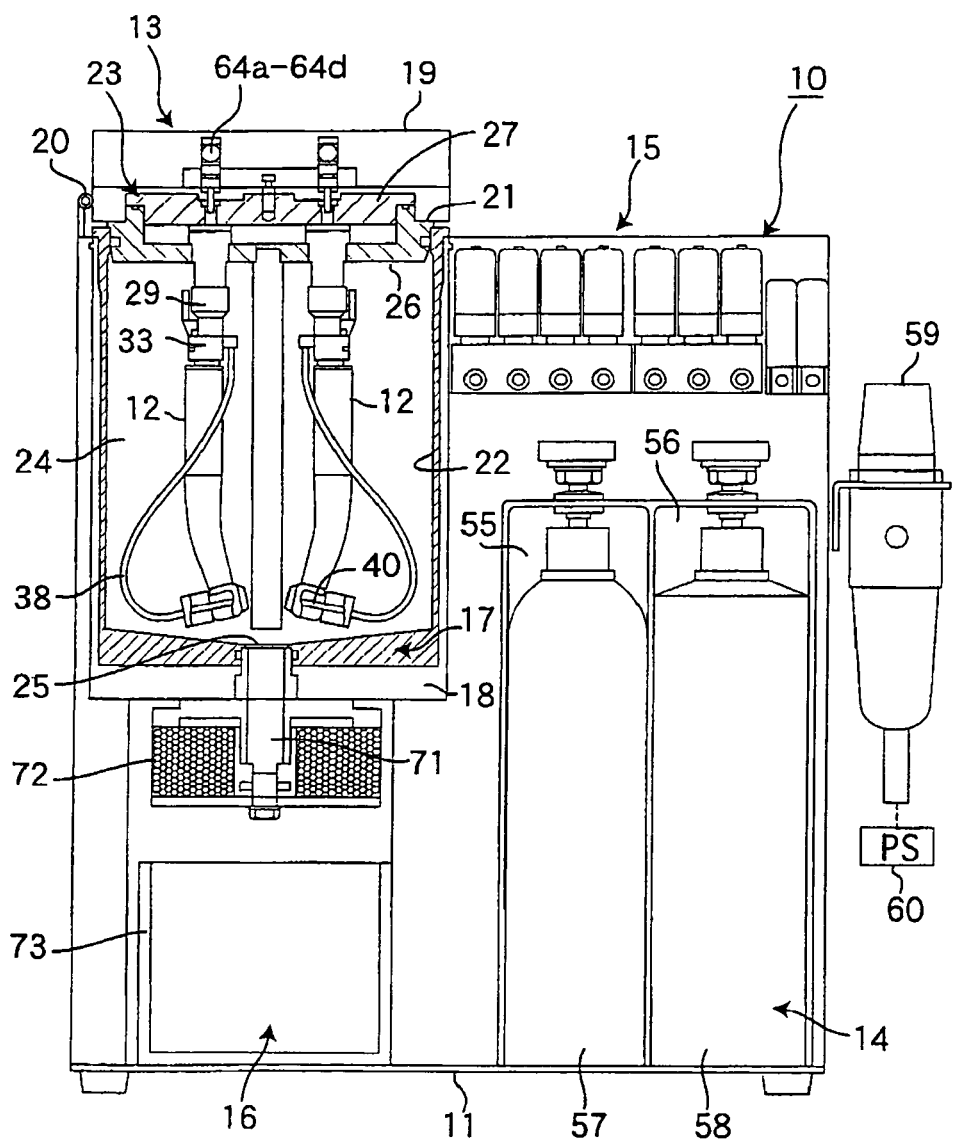
FIG. 2A is a sectional view of the apparatus shown in FIG. 1.

FIG. 1 and FIG. 2A show a maintenance apparatus according to the first embodiment of the present invention. The maintenance apparatus 10 has a metal or plastic housing 11. The housing 11 includes a holder section 13 for holding medical handpieces, for example, dental handpieces 12, a supply section 14 for supplying a maintenance fluid (e.g., a liquid, a gas or a mixture thereof) such as a washing liquid and a lubricant, a delivery section 15 for feeding the maintenance fluid from the supply section 14 to the handpieces 12 and controlling the feeding, and a recycling section 16 for collecting the maintenance fluid used for the washing of the handpieces 12.

(2) Holder Section

Figure 3:
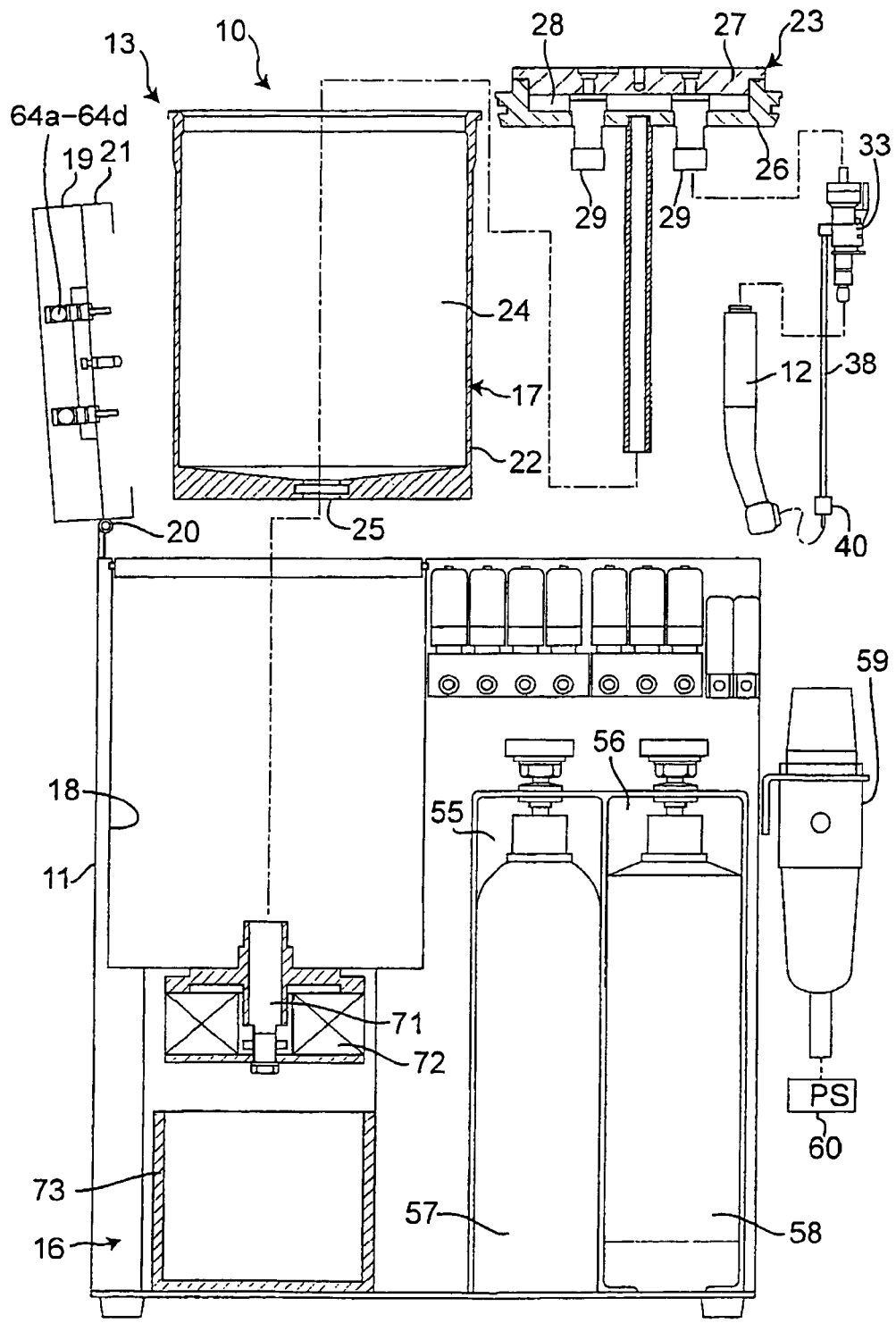
FIG. 3 is a diagram illustrating the disassembled apparatus shown in FIG. 2A.

The holder section 13 includes a container 17 for holding a plurality of handpieces 12. As shown in FIG. 3, the container 17 is removably inserted in the container-receiving chamber 18 formed from above in the housing 11. The holder section 13 has a lid 19 for opening or closing the upper opening of the container-receiving chamber 18. The lid 19 is rotatably supported by the housing 11 through a hinge 20, and is locked to the housing 11 in its closed state by a locking mechanism 21.

The container 17 includes a cylindrical container body 22 and a lid 23 for opening or closing the opening of the cylindrical container body 22. The cylindrical container body 22 has a cylindrical chamber 24 formed therein, and has a fluid outlet 25 formed at the center of the bottom. The surfaces of the cylindrical container body 22 and the lid 23, particularly the inner surfaces thereof, to which maintenance liquids such as a washing liquid and a lubricant tend to adhere, are coated with a water-repelling material such as polytetrafluoroethylene or the like. The lid 23 has such a size and shape as to seal the opening of the cylindrical container body 22. Preferably, the annular face of the lid 23 to contact the cylindrical container body 22 is provided with a sealing material such as a rubber O-ring so as to fully seal the chamber between the cylindrical container body 22 and the lid 23.

Figure 4:
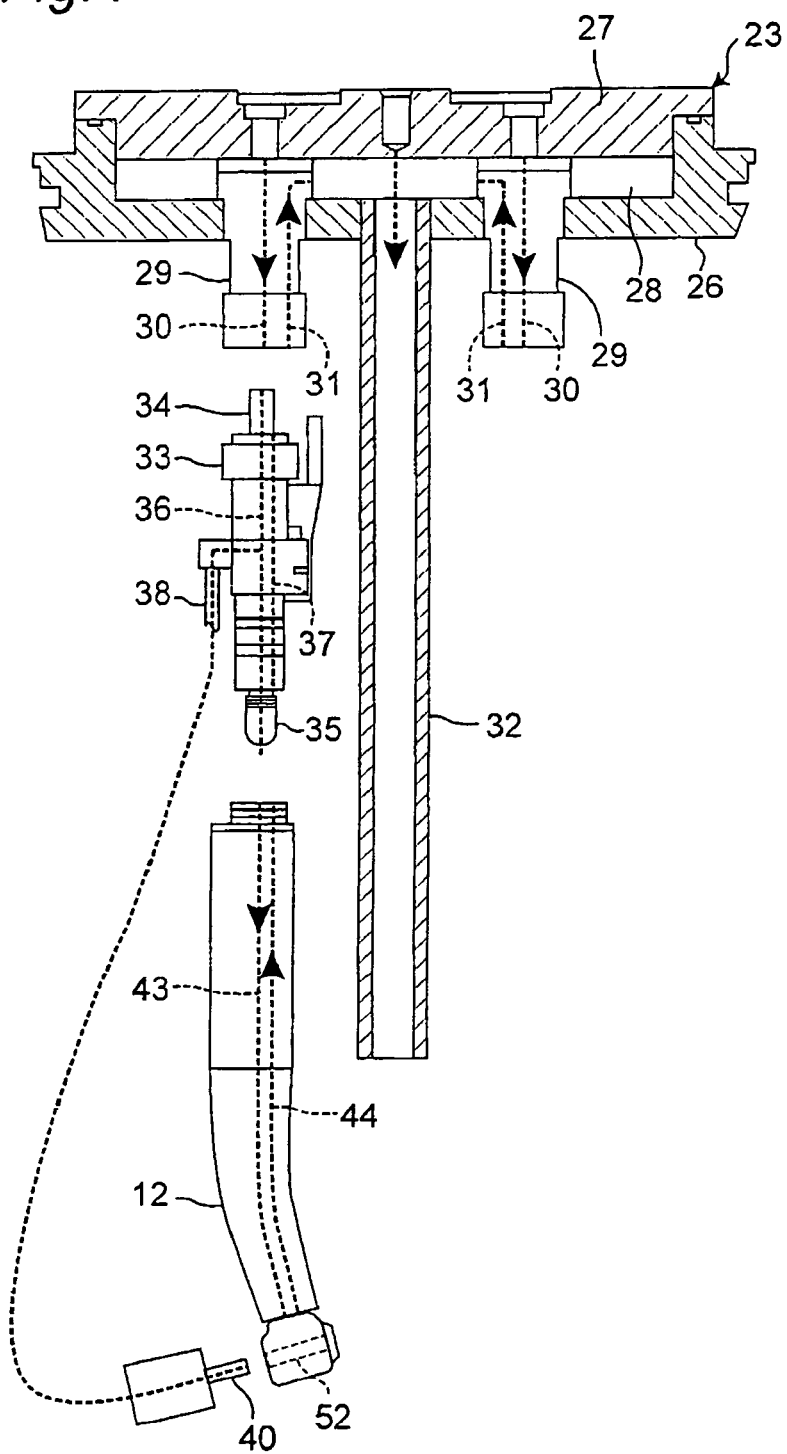
FIG. 4 is an enlarged diagram of a part of the apparatus shown in FIG. 2A.

As particularly shown in FIG. 4, the lid 23 consists of a lower lid 26 and an upper lid 27, and a sealed chamber 28 is formed between the lower lid 26 and the upper lid 27. A plurality of common adaptors 29 (four adaptors in this embodiment) are fixed on the circumference of the lower lid 26 which has a center on the vertical axis extending along the center of the lower lid 26. Each of the common adaptors 29 has two passages extending in parallel to the vertical axis (i.e., a first feeding passage 30 and a first recycling passage 31). The upper end of the first feeding passage 30 penetrates the upper lid 27 and is exposed at the surface of the upper lid 27, while the upper end of the first recycling passage 31 is opened to the sealed chamber 28. Further, a liquid-recycling tube 32 extending along the vertical axis is held at the center of the lower lid 26, and the upper end of the liquid-recycling tube 32 is communicated with the sealed chamber 28.

Figure 5A:
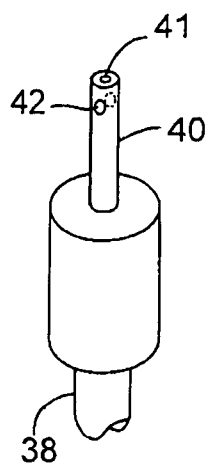
FIG. 5A is an enlarged perspective view of a nozzle.
Figure 5B:
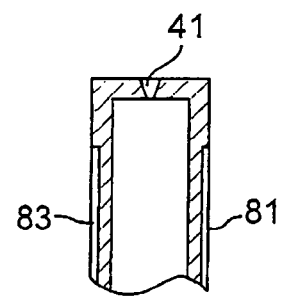
FIG. 5B is a sectional view of a nozzle of another type.
Figure 5C:
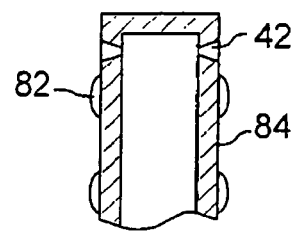
FIG. 5C is a sectional view of a nozzle of other type.
Figure 6:
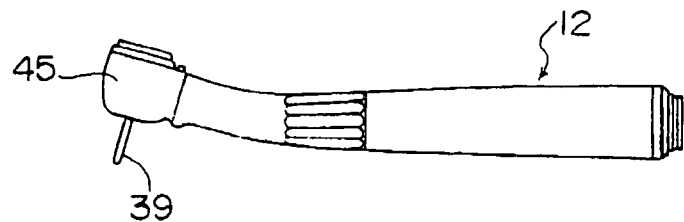
FIG. 6 is a side elevation of a dental handpiece.

An individual adaptor (or a connector) 33 having a connector corresponding to the type of the handpiece 12 is detachably attached to the lower end of the common adaptor 29. The individual adaptor 33 has a first connector 34 on the side of its proximal end, which is Lo be connected to the common adaptor 29, and a second connector (a first fluid supply) 35 on the side of its distal end, which is to be connected to the handpiece 12. Further, a second feeding passage 36 and a second recycling passage 37 extend between the first connector 34 and the second connector 35. When the individual adaptor 33 is attched to the common adaptor 29, the second feeding passage 36 and the second recycling passage 37 are connected to the first feeding passage 30 and the first recycling passage 31, respectively. Further, an elongated flexible tube (a second fluid supply) 38 is fixed at its one end to the substantial center between the first connector 34 and the second connector 35, and this tube 38 is connected to the second feeding passage 36. Further connected to the other end of the tube 38 is an elongated nozzle (a second fluid-feeding passage) 40 having an outer diameter substantially equal to that of a rotary cutting tool 39 (see FIG. 6) which is to be detachably attached to the handpiece 12. As shown in FIG. 5A, this nozzle 40 has injection holes 41 and 42 formed at its end face and outer peripheral wall, respectively, so that the maintenance fluid fed to the tube 38 is injected in the form of mist from the injection holes 41 and 42. While the injection holes 41 and 42 are formed in the end face and the outer peripheral wall of the nozzle 40 in this embodiment, it is also possible to form injection hole(s) in either of the end face and the outer peripheral wall of the nozzle, as shown in FIG. 5B or 5C.

Figure 7:
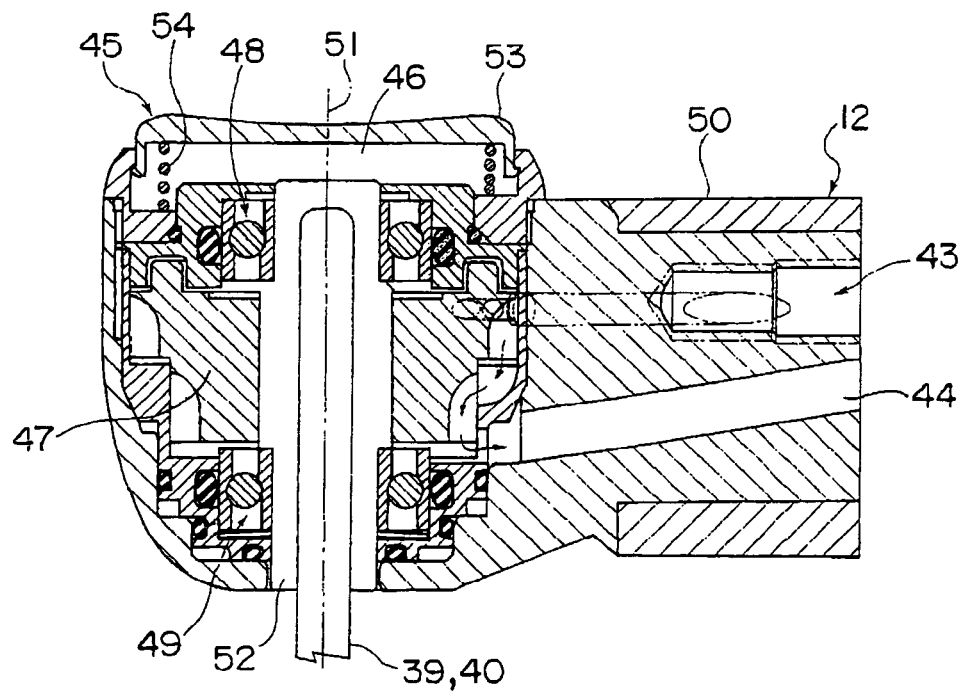
FIG. 7 is an enlarged diagram of a part of the handpiece shown in FIG. 6.

As shown in FIGS. 4 and 7, there are formed, in the handpiece 12, a third feeding passage 43 and a third recycling passage 44 corresponding to the second feeding passage 36 and the second recycling passage 37 of the individual adaptor 33, respectively. When the handpiece 12 is connected to a corresponding individual adaptor 33, the second feeding passage 36 is connected to the third feeding passage 43, and simultaneously, the second recycling passage 37 is connected to the third recycling passage 44. The handpiece 12 further has a rotatable member-housing chamber 46 at its head 45 on the side of the distal end thereof, as particularly shown in FIG. 7. The rotatable member-housing chamber 46 houses a rotatable member (a rotor and a turbine) 47 and bearings 48 and 49 supporting the rotatable member 47, and the rotatable member 47 is rotated on the rotation axis 51 as the center which orthogonally intersect the center axis of the gripping portion 50 of the handpiece (which an operator grips to hold the handpiece). The rotatable member 47 is provided with a chucking structure 52 which is located alongside the rotation axis 51, and a rotary cutting tool 39 is detachably inserted from the opening of one end (the lower end on the drawing) of the chucking structure 52. To unlock the chucking structure 52, a chuck-unlocking cover 53 is attached at the upper side of the rotatable member 47. When this cover 53 is pressed down against the force from a spring 54, the rotary cutting tool 39 held by the chucking structure 52 is released. As the structure of the chucking structure, any of the known chuck structures may be employed other than the so-called collet chuck: for example, the frictional force and elasticity of a resin or rubber may be utilized to hold a bar. The distal ends of the third feeding passage 43 and the third recycling passage 44 are exposed to the rotatable member-housing chamber 46 in the proximity of the outer peripheral wall of the rotatable member 47, respectively. While the handpiece 12 is used (or rotary cutting is performed), a compressed fluid fed through the third feeding passage 43 strikes the rotatable member 47 to rotate the same, and is then discharged through the third recycling passage 44.

(3) Supply Section

Again referring to FIG. 2A, the fluid supply 14 comprises a first container-receiving section 55 and a second container-receiving section 56, which are formed in the housing 11 and which house a first liquid supply container (a spray bomb) 57 and a second liquid supply container 58, respectively. An air filter 59 is attached to the side wall of the housing 11 so as to decompress a gas (or an air) supplied from a compressed air supply source 60, to a predetermined pressure.

(4) Delivery Section

The delivery section 15 comprises a control unit 280 (see FIG. 10) which controls the feeding of the maintenance fluid to the maintenance apparatus 10, and a circuit (see FIG. 8) which connects the liquid-supply containers 57 and 58 and the compressed air supply source 60 to the handpiece 12. The control unit 280 controls the feeding of the maintenance fluid to the chucking structure 52. The control unit 280 may be used to control not only the feeding of the maintenance fluid to the chucking structure but also the feeding of the maintenance fluid to the bearings 48 and 49. By doing so, the maintenance of all the parts of the handpiece can be automatically performed, so that effective and reliable maintenance of the handpiece can be realized. As seen in the circuit 84 shown in FIG. 8, an air passage (a pipe) 61 connected to the air filter 59 is equipped with a decompression device 62 in the vicinity of the proximal end thereof connected to the air filter 59, and the distal end portion of the pipe 61 is split into a plurality of air passing branched pipes 62a to 62d (four branched pipes in this embodiment) which are equipped with valves (electromagnetic valves) 63a to 63d, respectively, and which are connected at their distal ends to connectors 64a to 64d secured on the upper side of the lid 23, respectively. The connectors 64a to 64d are engaged with the common adaptors 29 and are connected thereto, when the lid 23 is closed (see FIG. 2A). Likewise, a liquid passage (a pipe) 65 connected to the first liquid-supply container 57 is equipped with a valve (an electromagnetic valve) 66, at and around its proximal end side connected to the container 57, and the distal end side of the pipe 65 is split into a plurality of liquid-passing branched pipes 67a to 67c (three branched pipes in this embodiment), which are equipped with valves (electromagnetic valves) 68a to 68c, respectively, and which are connected at their distal ends to the air passing branched pipes 62a to 62c and merged therewith, respectively, between the valves for the air (the electromagnetic valves) 63a to 63c and the connectors 64a to 64c. One liquid passage (a pipe) 69 connected to the second liquid supply container 58 is equipped with a valve (an electromagnetic valve) 70, at and around its proximal end side connected to the container 58, and is connected at its distal end side to the remaining air passing branched pipe 62d and merged therewith, between the valve 63d for the air and the connector 64d. Again referring to FIG. 8, a handpiece 12' is an air scaler handpiece which is not equipped with any rotary tool, namely, any chucking structure. Accordingly, a washing nozzle 40 is not needed for this handpiece, and therefore, the adaptor 33 corresponding to the handpiece 12' is not equipped with a washing nozzle.

Further again referring to FIG. 8, the circuit for feeding the maintenance fluid to the bearings of the handpiece 12 is not provided, and the maintenance fluid may be fed to only the chucking structure 52.

(5) Recycling Section

As shown in FIG. 2A and FIG. 3, the recycling section 16 has a connection pipe 71 which is vertically disposed in the lower side of the container-receiving chamber 18. The connection pipe 71 is connected to the liquid outlet 25 of the container 17 received in the container-receiving chamber 18. The lower end of the connection pipe 71 is connected to a filter 72 so that foreign matters contained in the fluid which drops through the connection pipe 71 can be captured by the filter 72. Further, a liquid-recycling container 73 is removably located under the filter 72 so as to collect the liquid which falls through the filter 72.

(6) Operation

The operation of the maintenance apparatus 10 thus arranged is described. As shown in FIGS. 2A and 3, the first liquid supply container 57 and the second liquid supply container 58 which hold liquids suitable for the washing and lubrication of the handpiece 12, respectively, are placed in the first container-receiving section 55 and the second container-receiving section 56 of the delivery section 15, respectively. For example, a plurality of manufactures provide lots of dental handpieces suitable for their own individual intensions and devices, and also provide containers for holding liquids of compositions optimal for the washing and the lubrication of their handpieces. Therefore, the liquid supply containers 57 and 58 suitable for the type of a handpiece which is needed for maintenance are placed in the corresponding container-receiving sections 55 and 56 and then are connected to the pipes. The air filter 59 is connected to the compressed air supply source 60.

Figure 2B:
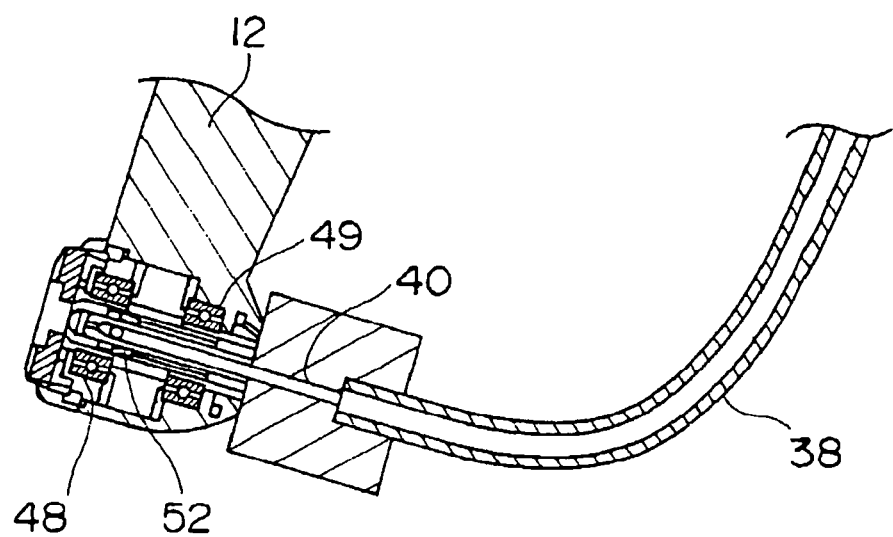
FIG. 2B is an enlarged diagram of a part of the apparatus shown in FIG. 2A.

Next, as shown in the deal drawing of FIG. 3, the lid 23 is removed from the holder section 13, and an individual adaptor 33 corresponding to the handpiece 12 is connected to the common adaptor 29, with the inner face of the lid 23 facing upward (turned upside down). Then, the handpiece 12 is connected at its proximal end to the individual adaptor 33 and secured thereto. As shown in FIG. 2B, the nozzle 40 attached to the distal end of the tube 38 is inserted in the chucking structure 52 and secured thereto. The nozzle 40 is attached in the same manner as in the attachment of the rotary cutting tool 39 to the handpiece 12, and is secured in the chucking structure 52 of the handpiece 12. Since the diameter and length of the rotary cutting tool differ according to the type of the handpiece, various kinds of nozzles 40 are prepared to thereby correspond to a variety of handpieces.

Figure 8:
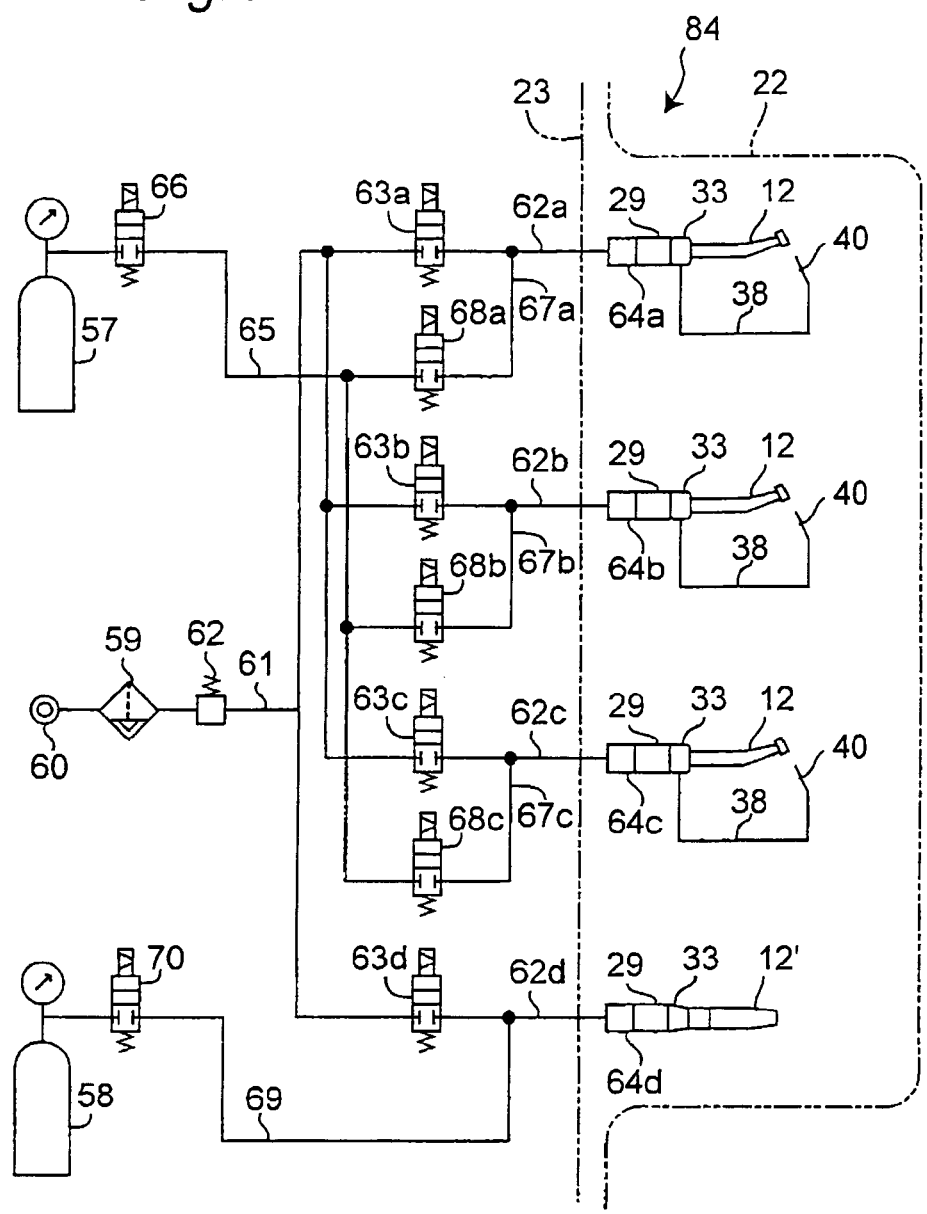
FIG. 8 is a circuit diagram of the apparatus shown in FIG. 2A.

The lid 23 equipped with these handpieces 12 is again turned upside down to face the handpieces 12 downward, and then, the lid 23 is placed on the opening of the upper end of the container 17 so that the handpiece 12 can be received in the container 17. Next, the lid 19 of the housing 11 is closed and fastened by the locking mechanism 21. Then, the connectors 64a to 64d secured on the lid 19 are connected to the common adaptors 29, so that the liquid supply containers 57 and 58 and the compressed air supply source 60 are connected to the handpieces 12 through the valves, as shown in FIG. 8.

Figure 9:
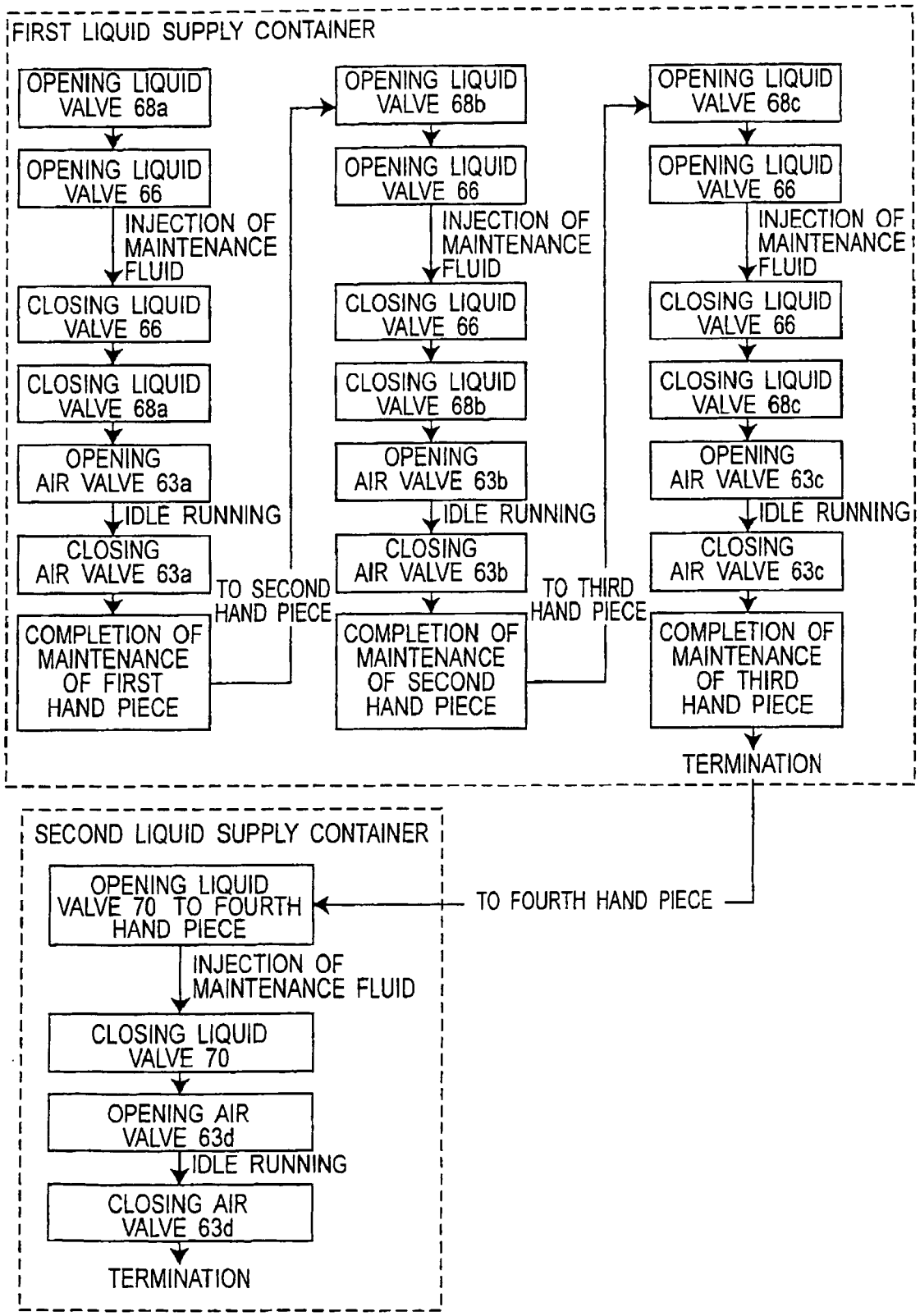
FIG. 9 is a flowchart for controlling the apparatus shown in FIG. 2A.
Figure 10:
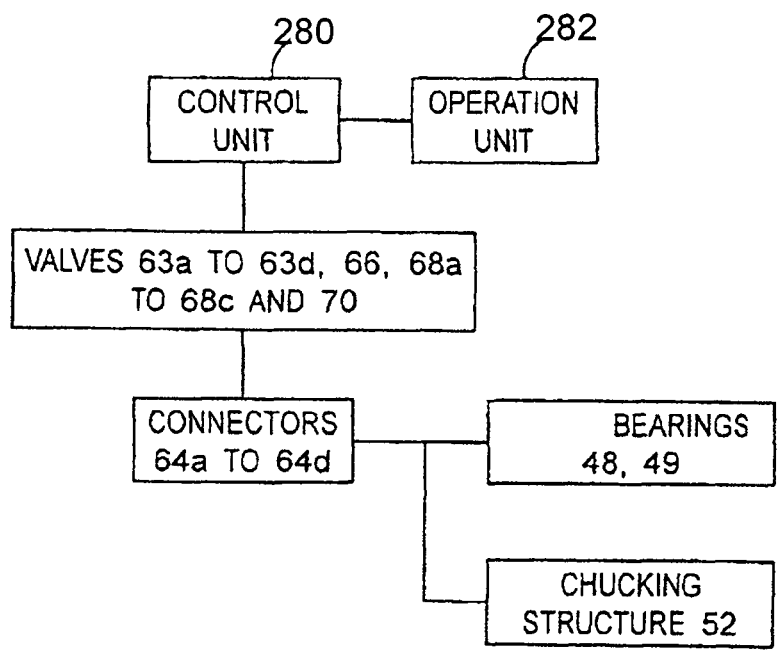
FIG. 10 is a block diagram for controlling the apparatus according to the first embodiment.

When the start switch (not shown) of the operation unit 282 shown in FIG. 10 is pressed down in this state, the valves 63a to 63d and the valves 68a to 68c provided on the branched pipes 62a to 62d and the branched pipes 67a to 67d which are connected the passages connected to the handpieces 12 are controlled to open or close, in response to a signal from the control unit 280, as shown in FIG. 9. As a result, the liquids (the washing liquid and the lubricant) supplied from the liquid supply containers 57 and 58 are mixed with a compressed air supplied from the compressed air supply source 60, and a mixture of these fluids is fed to the handpieces 12. Then, as shown in FIG. 4, a part of the fluid mixture is fed to the third feeding passage 43 formed in each of the handpieces 12, from the second feeding passage 36 formed in each of the individual adaptors 33, and is injected to the bearings 48 and 49 and the rotatable member 47 in the head of the handpiece, so as to wash off the foreign matters from the bearings 48 and 49 and the rotatable member 47 and lubricate them. While a part of the injected fluid mixture flows into a chamber between the bearings 48 and 49 and outgoes, most of the injected fluid mixture is finally led to the bottom of the container 17, after passing through the third recycling passage 44 in the handpiece 12, the second recycling passage 37 in the individual adaptor 33, the first recycling passage 31 in the common adaptor 29, the sealed chamber 28 of the lid 23 and the liquid-recycling pipe 32.

In the meantime, a part of the fluid mixture is injected in the form of mist from the injection holes 41 and 42 of the nozzle 40, into the chucking structure 59, after passing through the second feeding passage 36 of the individual adaptor 33 and the branched tube 38, so that the chucking structure 52 is washed and lubricated by the injected fluid mixture. Then, the fluid mixture injected into the chucking structure 52 flows around the nozzle 40 and goes out of the proximal end side of the nozzle 40 and drops into the bottom of the container 17. While the pressure of the fluid fed from the third feeding passage 43 imparts a turning force to the rotatable member 47, the nozzle 40 held by the chucking structure 52 formed integrally with the rotatable member 47 is unrotatable, so that the rotatable member 47 is not rotated.

The fluid which has dropped into the bottom of the container 17 is collected in the liquid outlet 25 at the center of the bottom, flowing along the conically shaped bottom, and is fed to the filter 72 through the connection tube 71. The fluid is then filtered to remove the foreign matters, and is collected in the liquid-recycling container 73.

In this connection, when a groove 81 or a ridge 282 is formed on the outer wall of the nozzle 40 as shown in FIG. 5B or 5C, a passage 83 or 84 along which the fluid flows to the proximal end of the nozzle 40 is formed between the outer wall of the nozzle 40 and the inner wall of the chucking structure 52. By doing so, the fluid is caused to more smoothly flow along the passage 83 or 84. Therefore, the efficient feeding and discharge of the fluid becomes possible, and the washing effect by the fluid is improved.

Further, the opening of the valves 63a to 63d, 66, 68a to 68c and 70 may be periodically changed by the control unit shown in FIG. 10. In this case, the pressure of the fluid injected to the bearings 48 and 49 and the chucking structure 52 is periodically changed, and therefore, the washing effect is more improved.

FIG. 9 shows an example of the controlling methods for performing the maintenance of every one of handpieces, using the maintenance apparatus 10 having the circuit shown in FIG. 8. In this method, the number of the valves is increased or decreased to thereby simultaneously perform maintenance on a plurality of handpieces, or to thereby perform maintenance on the bearings 48 and 49 and the chucking structure 52 at different timing.

After the completion of the washing and lubrication of the handpieces, the liquid valves 66, 68a to 68c and 70 are closed, and then, an air only is fed to the handpieces for idle running so as to remove the excessive maintenance fluid. After that, the air valves 63a to 63d are closed to inhibit the feeding of all the liquids and air. The air for idly running the handpieces may be continuously or discontinuously fed under the control by the control unit. When the air is discontinuously fed, the excessive maintenance fluid can be more effectively removed. Next, the locking mechanism 21 is unlocked to open the lid 19, and then, the container 17 and the lid 23 are removed from the container-receiving section 18. The nozzles 40 are detached from the handpieces 12 with the lid 23 turned upside down, and the handpieces 12 are removed from the lid 23 so as to remove the moisture. Further, the individual adaptors 33 are removed from the lid 23. Then, the interior surface of the container 17, the lid 23 and the individual adaptors 33 are washed.

As described above, the maintenance apparatus 10 washes and lubricates the handpieces 12 while preventing the injected fluid mixture from flying out from the container 17, by confining the handpieces 12 within the container 17 which is perfectly sealed except for the liquid outlet 25. Therefore, it becomes possible to keep the maintenance apparatus 10 in a clean condition.

Further, the handpiece 12 is washed and lubricated at not only its bearings 48 and 49 but also its chucking structure 52 with the maintenance fluid. Therefore, the abrasion filing left to remain in the chucking structure 52 can be completely removed. Consequently, not only the the duration of the chucking structure 52 but also the the duration of the handpiece 12 become longer.

Furthermore, the apparatus 10 can be used corresponding to a handpiece having optional shape and size, by using an individual adaptor (a connector) 33. Therefore, it becomes possible for one maintenance apparatus 10 to concurrently perform maintenance on various types of handpieces 12 which are provided by different manufacturers, by preparing individual adaptors 33 corresponding to the types of such handpieces.

The application of the present invention is not limited by the type of the bearings 48 and 49 of the handpiece. For example, the present invention can be applied to not only handpieces having ball bearings but also handpieces having pneumatic bearings (fluid bearings).

Further, the maintenance liquids for the handpieces are not limited to specific types of liquids or gases, and various materials can be used. While the maintenance liquids are charged in the spray bombs in the foregoing embodiment, it is also possible to house a container charged with a liquid separately from a container charged with a gas for injection, or otherwise, it is also possible to use a compressed air instead of a gas.

Furthermore, the compressed air and the washing liquid may be intermittently fed at the same time intervals or different time intervals, or the feeding forces thereof may be increased or decreased.

Still furthermore, the nozzle 40 is designed not to rotate in the embodiment, and therefore, the chucking structure 52 holding this nozzle 40 and the rotatable member 47 are not rotated. However, the nozzle 40 may be rotatably combined with the tube 38 through a swivel joint to allow the rotatable member 47 and the chucking structure 52 to rotate together with the nozzle 40 during the maintenance.

The embodiment of the present invention can be applied to not only handpieces driven by a compressed air but also handpieces driven by electric motors.

II. Second Embodiment

Figure 11:
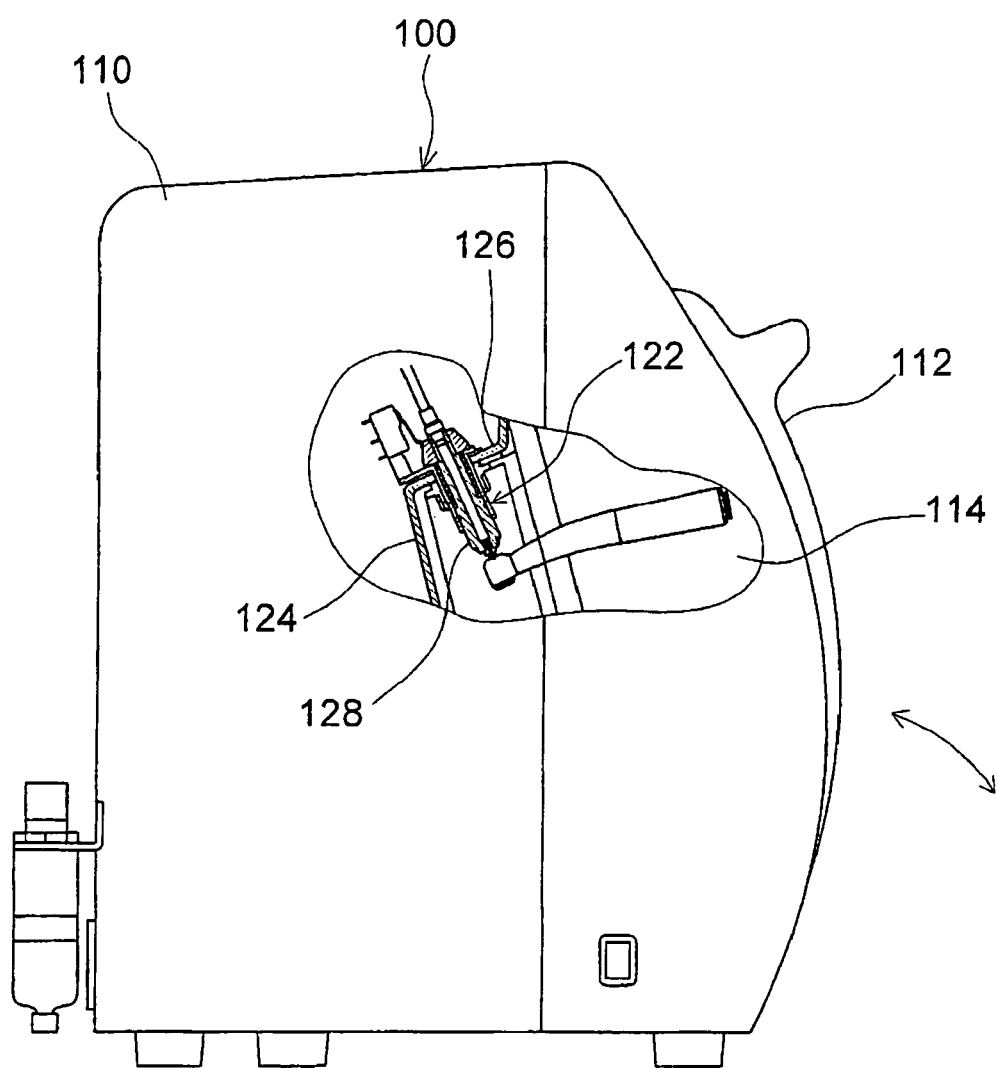
FIG. 11 is a side elevation of a maintenance apparatus according to the second embodiment of the present invention.

A maintenance apparatus according to the second embodiment of the present invention is shown in FIG. 11. The maintenance apparatus 100 shown in FIG. 11 is covered with a housing 110 having a door 112 at its front side. In this embodiment, the door 112 is hinged at its lower end to the housing 110, and is opened or closed in the directions indicated by arrows.

Figure 12:
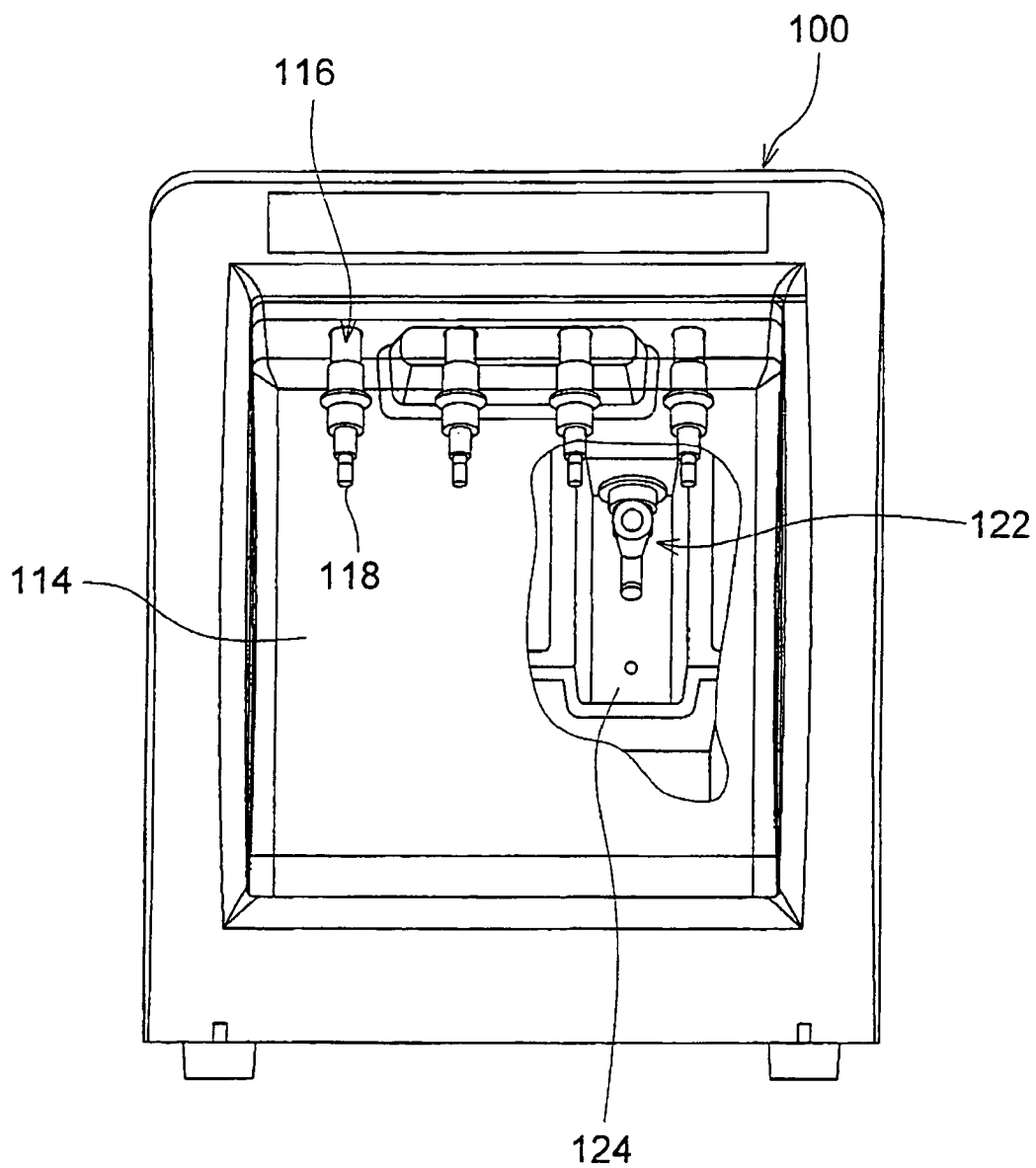
FIG. 12 is a front view of the apparatus shown in FIG. 11.

As shown in FIG. 12, a holder chamber 114 for holding handpieces for maintenance is formed inside the door 112. The holder chamber 114 includes a first fluid supply 116 which supplies a maintenance fluid to the bearings of the handpieces, and a second fluid supply 122 which supplies a maintenance fluid to the chucking structures of the handpieces. The first fluid supply 116 has a plurality of adaptors 118 (four adaptors in this embodiment). In this embodiment, the plurality of adaptors 118 are of the same type as that of the adaptors 29 of the first embodiment, and are mounted on the ceiling 120 of the holder chamber 114. Referring again to FIG. 11, the second liquid supply 122 is provided in a chamber 124 which is formed by widening the holder chamber 144 toward the rear side and which has an adaptor 128 fixed on its ceiling 126.

Figure 13:
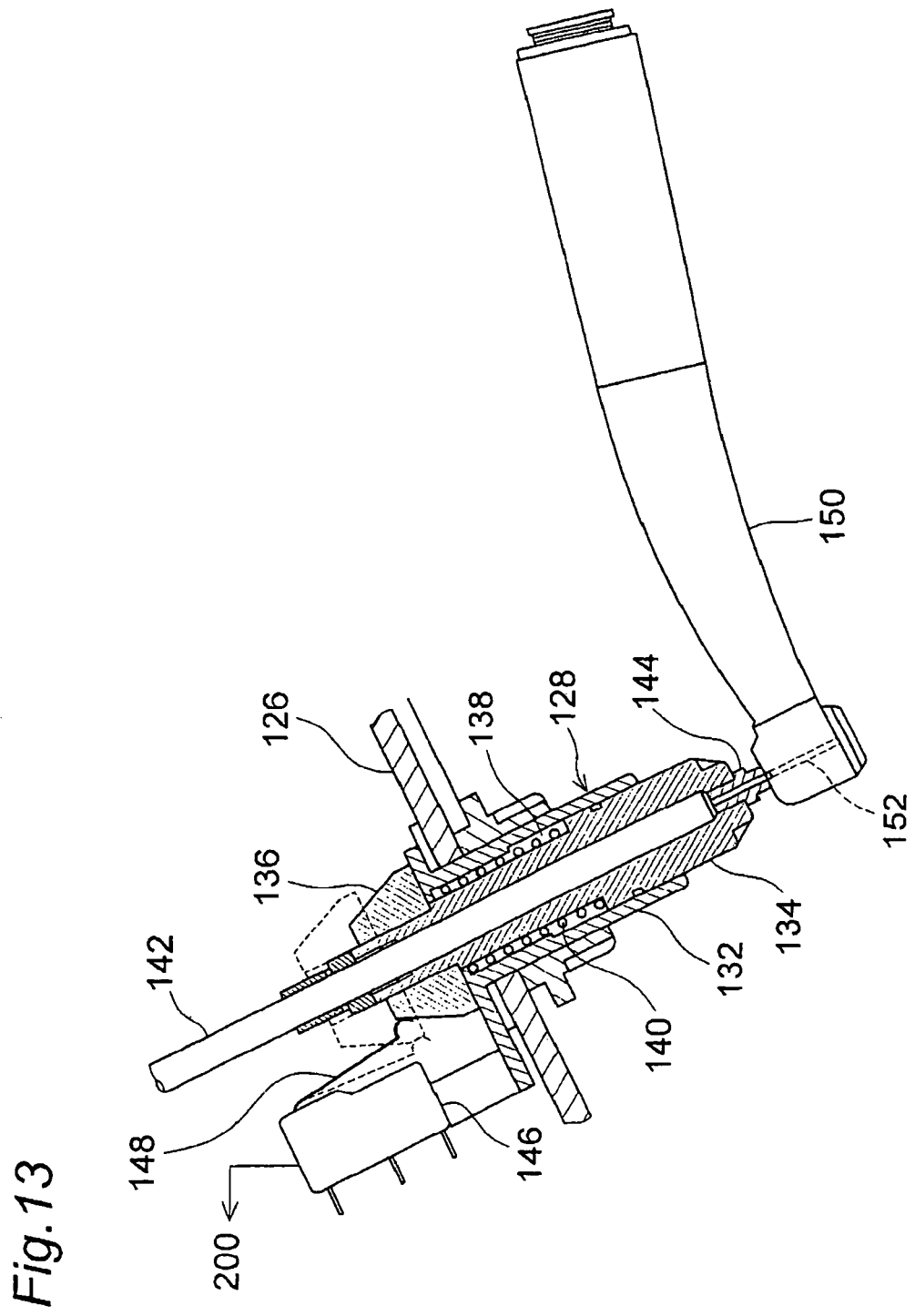
FIG. 13 is a sectional view of an adaptor for the second fluid supply.

As shown in FIG. 13, the adaptor 128 has an outer housing 132 fixed to the ceiling 126. The inner housing 134 is fitted in the outer housing 132, penetrating the same and the ceiling 126, and an operation ring 136 is mounted on a part of the inner housing 134 on the reverse side of the ceiling 126. A helical spring 140 is disposed in an annular chamber 138 formed between the outer housing 132 and the inner housing 134. This spring 140 urges the inner housing 134 downward. A nozzle 144 which is to be inserted in the chucking structure 152 of a handpiece 150 and held thereby is attached to the lower end portion of the inner housing 134 located inside the chamber 124, and a feeding pipe 142 for the maintenance fluid is connected to the upper end portion of the inner housing 134 which is located outside the chamber 124.

A limit switch 146 is fixed on the reverse side of the ceiling 126, and a contact point-opening or -closing member (a contact point-opening or -closing lever) 148 of the limit switch is allowed to contact the operation ring 136. When the inner housing 134 is pushed upward against the force from the spring 140, the operation ring 136 is moved upward together with the inner housing 134, and the contact point-opening or -closing member 148 is moved from the position drawn by the solid line to a position drawn by the dotted line to turn on the switch 146. When the force applied to the inner housing 134 in this state is eliminated, the inner housing 134 is returned to the position drawn on the figure, and the switch 146 is turned off.

The switch 146 is connected to a control unit 200 which is of the same type as that of the control unit 280 described in the first embodiment, and the control unit 200 decides whether or not the handpiece 150 is connected to the second fluid supply 122, based on a signal transmitted from the switch 146.

Figure 14:
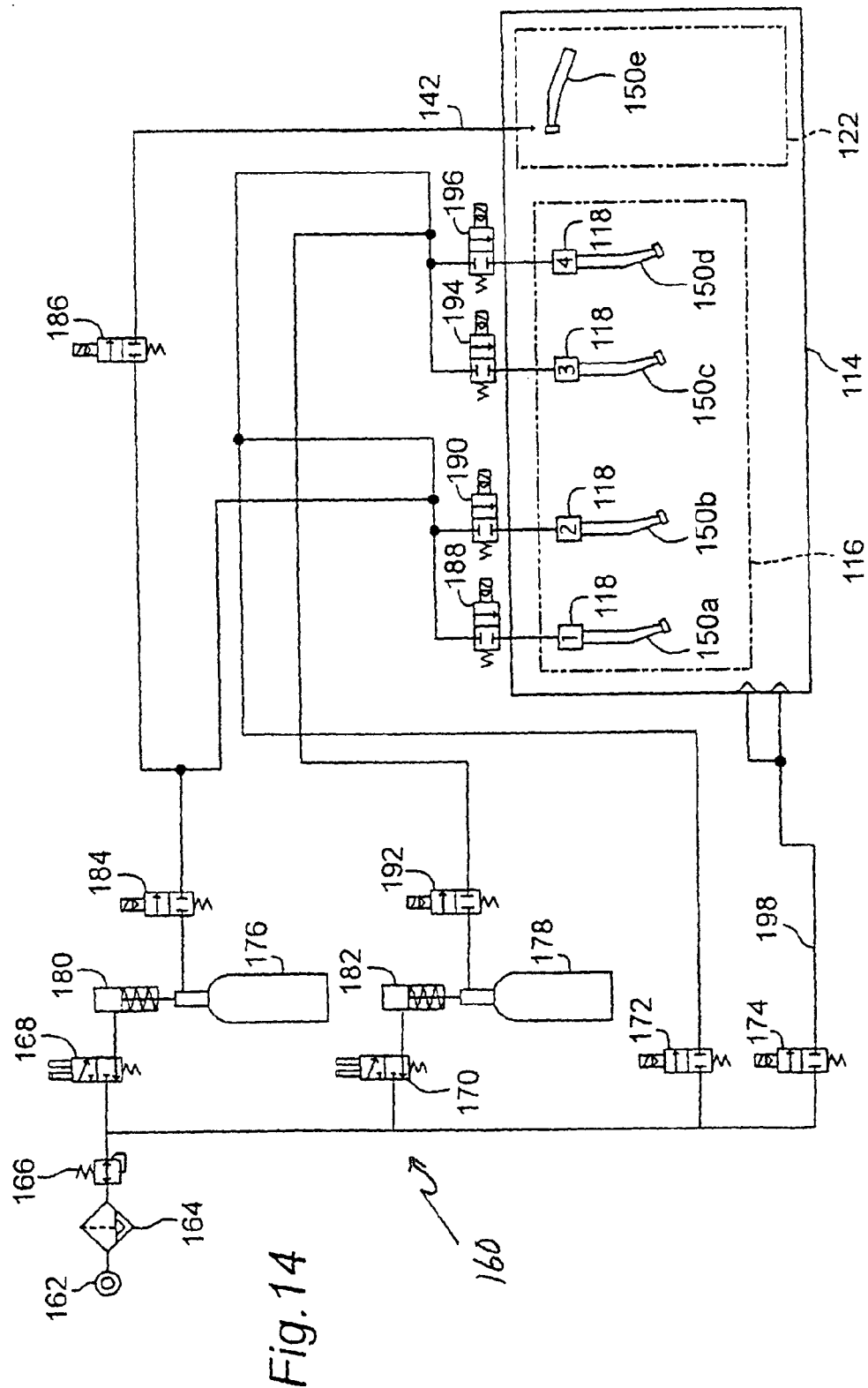
FIG. 14 is a circuit diagram of the apparatus shown in FIG. 11.

FIG. 14 shows a fluid circuit 160 which feeds the maintenance fluid to the first fluid supply 116 and the second fluid supply 122. In this circuit 160, the compressed air supply source 162 is connected to a plurality of electromagnetic valves 168, 170, 172 and 174 through an air filter 164 and a decompression device 166. The electromagnetic valves 168 and 170 arc connected to the valves 180 and 182 of the fluid-supply containers 176 and 178, respectively, so that the valves 180 and 182 can be opened or closed by the electromagnetic valves 168 and 170. The fluid-supply container 176 is connected to the fluid-feeding pipe 142 of the second fluid supply 122, through the electromagnetic valves 184 and 186. The fluid-supply container 176 is connected to the adaptors 118 (118*a*, 118*b*) of the first fluid supply 116, via the electromagnetic valve 184 and further via the electromagnetic valves 188 and 190. The other fluid-supply container 178 is also connected to the adaptors 118 (118*c*, 118*d*) of the first fluid supply 116 via the electromagnetic valve 192 and further via the electromagnetic valves 194 and 196. The electromagnetic valve 172 is connected to the electromagnetic valves 188, 190, 194 and 196, and the electromagnetic valve 174 is connected to an air blow tube 198 connected to the holder chamber 114.

The electromagnetic valves 168 to 174 and 184 to 196 included in the circuit 160 thus arranged are electrically connected to the control unit 200, and are operated as follows according to the program stored in the control unit 200.

Figure 15:
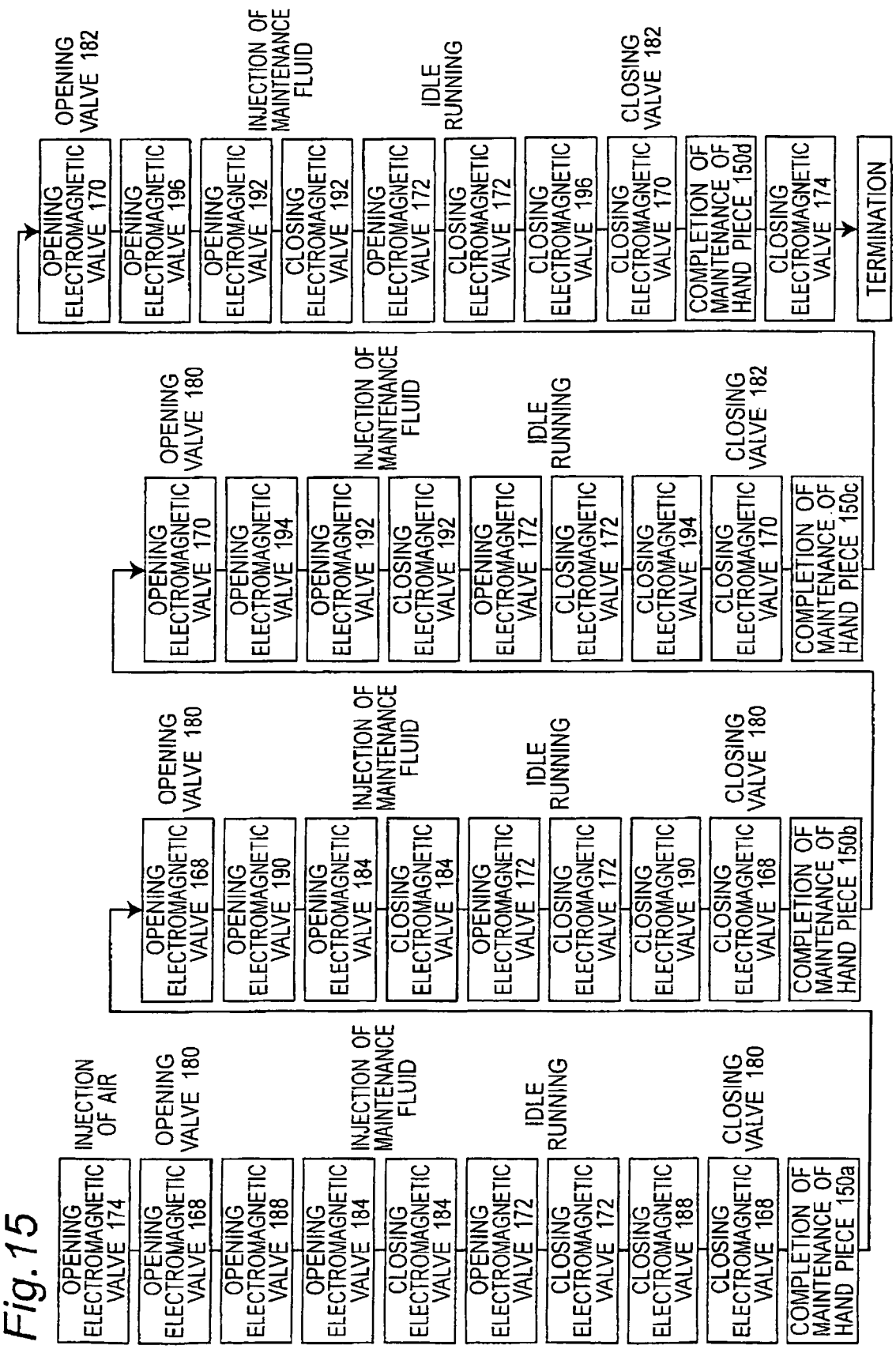
FIG. 15 is a flowchart for controlling the first fluid supply of the apparatus according to the second embodiment.

For example, when handpieces 150 (150*a* to 150*d*) are connected to the four adaptors 118 of the first fluid supply 116, respectively, as shown in FIG. 14, the maintenance fluid is sequentially fed to these four handpieces 150 for the treatment thereof. This is described in detail with reference to FIG. 15. When the start switch (not shown) of the operation unit 82 is pressed down, the control unit 200 firstly opens the electromagnetic valve 174 to thereby release an air into the holder chamber 114 from the compressed air supply source 162 through the air blow tube 198. Next, the control unit 200 operates the electromagnetic valve 168 to open the valve 180 so as to feed the maintenance fluid from the fluid-supply container 176. Next, the control unit 200 opens the electromagnetic valve 188 and opens the electromagnetic valve 184 for a predetermined time in this state, to thereby feed the maintenance fluid from the fluid-supply container 176 to the handpiece 150*a*. The maintenance fluid thus fed passes through the fluid passage and the bearings of the handpiece 150*a*, and the fluid discharge passage, and falls into the holder chamber 114 to be recycled. After that, the control unit opens the electromagnetic valve 172 for a predetermined time to thereby feed the compressed air to the washed handpiece 150*a* so as to discharge the liquid left to remain in the handpiece 150*a*. Then, the control unit closes the electromagnetic valve 188, and operates the electromagnetic valve 168 to close the valve 180 of the fluid-supply container 176. Thus, the treatment of the first handpiece 150*a* is completed.

The second handpiece 150*b* is treated in the same manner as in the treatment of the first handpiece 150*a*, except that another electromagnetic valve 190 connected to the second handpiece 150*b* is opened or closed, instead of the electromagnetic valve 188 connected to the first handpiece 150*a*.

In this embodiment, the maintenance fluid is fed from another fluid-supply container 178, to the third and fourth handpieces 150*c* and 150*d*. This is described in detail. The control unit 200 operates the electromagnetic valve 170 to open the valve 182, so that the maintenance fluid can be fed from the fluid-supply container 178. Next, the control unit 200 opens the electromagnetic valve 194, and opens the electromagnetic valve 192 for a predetermined time in this state, to thereby feed the maintenance fluid to the handpiece 150*c* from the fluid-supply container 178. The maintenance fluid thus fed passes through the fluid-feeding passage and the bearings of the handpiece 150*c* and falls into the holder chamber 114 from the fluid discharge passage, and is recycled. After that, the control unit opens the electromagnetic valve 172 for a predetermined time to feed the compressed air to the washed handpiece 150*c* to thereby discharge the liquid left to remain in the handpiece 150*c*. Then, the control unit closes the electromagnetic valve 194 and operates the electromagnetic valve 170 to close the valve 182 of the liquid-supply container 178. Thus, the treatment of the third handpiece 150*c* is completed.

The fourth handpiece 150*d* is treated in the same manner as in the treatment of the third handpiece 150*c*, except that another electromagnetic valve 196 connected to the fourth handpiece 150*d* is opened or closed, instead of the electromagnetic valve 194 connected to the third handpiece 150*c*. When this treatment is completed, the electromagnetic valve 174 is closed to thereby complete the release of the air into the holder chamber 114.

Figure 16:
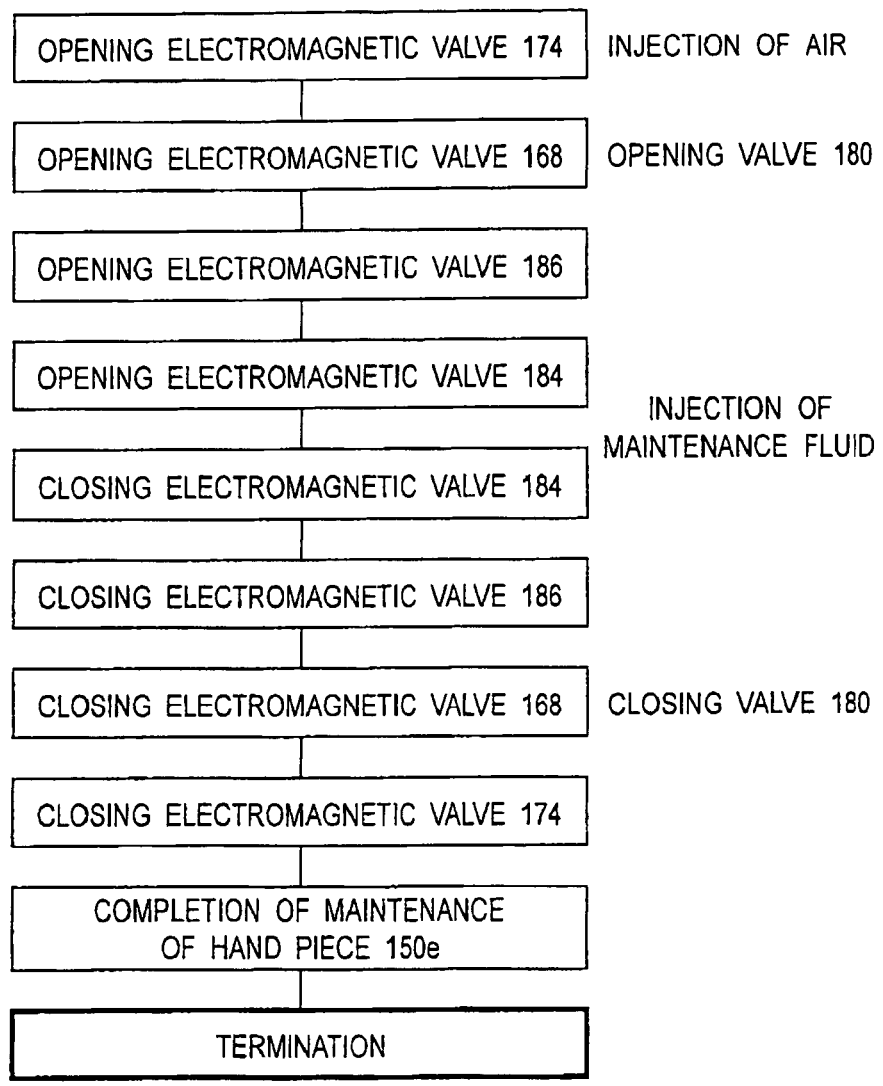
FIG. 16 is a flowchart for controlling the second fluid supply of the apparatus according to the second embodiment.

The maintenance of the chucking structure of the handpiece 150*e* connected to the adaptor 128 of the second fluid supply 122 is described below. When an operator pushes up the handpiece 150*e* connected to the adaptor 128 to turn on the switch 146, or when the switch 146 is kept to be turned on over a predetermined time, the control unit 200 opens the electromagnetic valve 174 to release the air into the holder chamber 114 through the air blow tube 198 from the compressed air supply source 162, as shown in FIG. 16. Next, the control unit 200 operates the electromagnetic valve 168 to open the valve 180 so that the maintenance fluid can be fed from the fluid-supply container 176. Next, the control unit 200 opens the electromagnetic valve 186 and opens the electromagnetic valve 184 for a predetermined time in this state to thereby feed the maintenance fluid to the chucking structure of the handpiece 150*e* from the fluid-supply container 176. The maintenance fluid discharged from the handpiece 150*e* is allowed to fall into the holder chamber 114 to be recycled. After that, the control unit 200 closes the electromagnetic valve 186 and then operates the electromagnetic valve 168 to close the valve 180 of the fluid-supply container 176. Finally, the control unit closes the electromagnetic valve 174 to thereby complete the release of the air into the holder chamber 114. The attaching of the handpiece 150*e* to the second fluid supply 122 is detected based on a signal transmitted from the switch 146 to the control unit 200.

The maintenance apparatus 100 according to this embodiment also includes a recycling container for recycling the maintenance fluid used for the treatment, although the recycling container is not shown in the drawings. Thus, the maintenance fluid collected in the holder chamber 114 is recycled to the recycling container.

Also, the maintenance apparatus according to the second embodiment may be various modified, and all the examples of the modification described in connection with the first embodiment can be applied to the maintenance apparatus according to the second embodiment.

In the foregoing description, the maintenance relative to the second fluid supply 122 is started in response to a ON signal from the switch 146. Alternatively, for example, a self-holding type switch may be used as the switch 146. When the start switch of an operation unit (not shown) is turned on while this self-holding type switch is being turned on, the control unit 200 automatically starts the maintenance on the handpiece 150*e* attached to the second fluid supply 122 described above. The attaching of the handpiece 150*e* to the second fluid supply 122 can be detected by a switch of another type; or otherwise, by utilizing the conductive material portion of the handpiece, it becomes possible to transmit a detection signal to the control unit through this conductive material portion of the handpiece which is correctly attached to the second fluid supply 122. Further, the handpieces may be attached to the first fluid supply 116 and the second fluid supply 122 in optional directions.

The invention claimed is:

1. A maintenance apparatus for a medical handpiece with a chucking structure for detachably chucking and holding a rotary tool along an axis and a bearing for rotatably supporting the chucking structure along the axis; comprising:
   a maintenance fluid supply nozzle fluidly connected to a second fluid supply, said maintenance fluid supply nozzle being designed so as to be detachably connected to a chucking structure in place of a rotary tool so that the maintenance fluid is fed through the nozzle into the chucking structure.

2. The maintenance apparatus of claim 1, further comprising a first fluid supply for feeding the maintenance fluid to a bearing of the handpiece.

3. The maintenance apparatus of claim 2, further comprising a connector which is so designed that a handpiece is detachably connected to the connector, the connector having a feeding passage of the first fluid supply for feeding the maintenance fluid through the first feeding passage to the bearing of the handpiece and a feeding passage of the second fluid supply for feeding the maintenance fluid through the nozzle to the chucking structure.

4. The maintenance apparatus according to any one of claims 1 to 3, wherein the nozzle has at least one hole for injecting the maintenance fluid in the form of mist.

5. The maintenance apparatus according to claim 1, wherein said maintenance fluid supply nozzle comprises an elongated nozzle having an outer diameter substantially equal to an outer diameter of said rotary tool, said elongated nozzle having one end portion for insertion into said chucking structure and another end portion for being coupled to said second fluid supply.

* * * * *

UNITED STATES PATENT AND TRADEMARK OFFICE
CERTIFICATE OF CORRECTION

| | | |
|---|---|---|
| PATENT NO. | : 8,439,677 B2 | Page 1 of 1 |
| APPLICATION NO. | : 10/565769 | |
| DATED | : May 14, 2013 | |
| INVENTOR(S) | : Makoto Numakawa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 939 days.

Signed and Sealed this
Ninth Day of December, 2014

Michelle K. Lee
*Deputy Director of the United States Patent and Trademark Office*